United States Patent [19]

Mais et al.

[11] Patent Number: 5,684,217
[45] Date of Patent: Nov. 4, 1997

[54] PROCESS FOR PREPARING 3-FLUORO-4,6-DICHLOROTOLUENE

[75] Inventors: Franz-Josef Mais, Düsseldorf; Werner Bussmann; Helmut Fiege, both of Leverkusen, all of Germany

[73] Assignee: Bayer Aktiengesellschaft, Leverkusen, Germany

[21] Appl. No.: 572,229

[22] Filed: Dec. 13, 1995

[30] Foreign Application Priority Data

Dec. 20, 1994 [DE] Germany ............... 44 45 548.8

[51] Int. Cl.⁶ ............................................. C07C 22/00
[52] U.S. Cl. ............................................. 570/147
[58] Field of Search ............................... 570/147

[56] References Cited

U.S. PATENT DOCUMENTS

| | | |
|---|---|---|
| 3,388,174 | 6/1968 | Crosbie et al. .......... 570/147 |
| 4,417,081 | 11/1983 | Soula ..................... 570/147 |
| 4,439,620 | 3/1984 | Klauke et al. . |
| 4,851,596 | 7/1989 | Mais et al. . |
| 4,925,994 | 5/1990 | Mais et al. . |
| 4,990,707 | 2/1991 | Mais et al. . |
| 5,105,036 | 4/1992 | Mais et al. . |
| 5,475,164 | 12/1995 | Bussmann . |

FOREIGN PATENT DOCUMENTS

| | | |
|---|---|---|
| 0114604A1 | 8/1984 | European Pat. Off. . |
| 0114604B1 | 8/1984 | European Pat. Off. . |
| 0126669 | 11/1984 | European Pat. Off. . |
| 0292824 | 11/1988 | European Pat. Off. . |
| 0340581 | 11/1989 | European Pat. Off. . |
| 0368063 | 5/1990 | European Pat. Off. . |
| 0442115 | 8/1991 | European Pat. Off. . |
| 0657407 | 6/1995 | European Pat. Off. . |
| 2545004 | 11/1984 | France . |
| 3142856 | 5/1983 | Germany . |

*Primary Examiner*—Alan Siegel
*Attorney, Agent, or Firm*—Sprung Kramer Schaefer & Briscoe

[57] ABSTRACT

3-Fluoro-4,6-dichlorotoluene can be prepared in a particularly favourable manner by first chlorinating 3-fluorotoluene at low temperature in the presence of a Friedel-Crafts catalyst and a heterocyclic cocatalyst to give a mixture containing 3-fluoro-4-chlorobenzene and 3-fluoro-6-chlorobenzene, and subsequently, without intermediate isolation, further chlorinating this mixture, at higher temperature, after addition of further Friedel-Crafts catalyst and further heterocyclic cocatalyst, to give 3-fluoro-4,6-dichlorotoluene.

7 Claims, No Drawings

PROCESS FOR PREPARING 3-FLUORO-4,6-DICHLOROTOLUENE

The present invention relates to an improved process for preparing 3-fluoro-4,6-dichlorotoluene by selective chlorination of 3-fluorotoluene with reduced formation of the byproduct 3-fluoro-2,6-dichlorotoluene.

3-Fluoro-4,6-dichlorotoluene is an important intermediate for the preparation of pharmaceutically active compounds of the quinolonecarboxylic acid type.

A series of synthetic routes have been described for the preparation of 3-fluoro-4,6-dichlorotoluene which require special expense owing to their multistage nature and/or they involve using materials which can be handled only with difficulty in industry.

It is known that 3-fluoro-4,6-dichlorotoluene can be prepared from 3-amino-4,6-dichlorotoluene via the steps diazotization, coupling with dimethylamine, reaction with hydrogen fluoride and thermal dissociation (see German Offenlegungsschrift 3 142 856). Although this gives good yields in the last step, the preparation involves 4 reaction stages and the handling of a triazene compound which decomposes easily.

A process has now been found for preparing 3-fluoro-4,6-dichlorotoluene, which is characterized in that 3-fluorotoluene is first chlorinated at low temperature in the presence of a Friedel-Crafts catalyst and a heterocyclic cocatalyst to give a mixture containing 3-chloro-4-chlorotoluene and 3-chloro-6-chlorotoluene, and this mixture is subsequently, without intermediate isolation, further chlorinated at higher temperature, after addition of further Friedel-Crafts catalyst and further heterocyclic cocatalyst, to give 3-fluoro-4,6-dichlorotoluene.

Suitable Friedel-Crafts catalysts for both reaction stages of the process of the invention are, for example, metal and transition metal halides. Preference is given to iron(III) chloride, antimony(III) chloride, antimony(V) chloride and aluminium chloride; particular preference is given to iron (III) chloride. Identical or different Friedel-Crafts catalysts can be used in the two reaction stages. Preference is given to using the same Friedel-Crafts catalyst in both reaction stages.

In the first reaction stage, for example, from 0.05 to 1% by weight of Friedel-Crafts catalyst (based on 3-fluorotoluene) can be used. This amount is preferably from 0.2 to 1% by weight. In the second reaction stage, for example, a further 0.1 to 5% by weight of Friedel-Crafts catalyst (based on 3-fluorotoluene) can be added. This additional amount is preferably from 0.5 to 2% by weight.

The cocatalysts used for the two reaction stages of the process of the invention can be, for example, heterocycles which contain both N and S atoms and belong, for example, to the classes of thiazines, thiazepines or thiazocines. Examples which may be mentioned are:

Thiazepines of the formulae

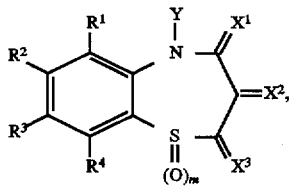

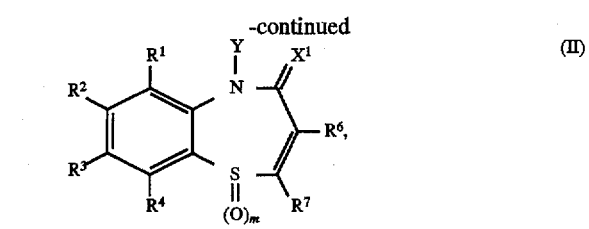

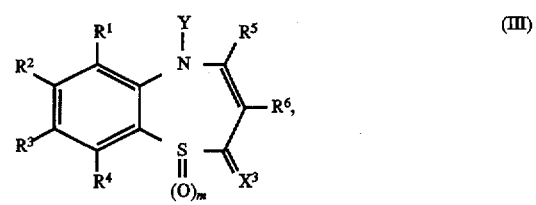

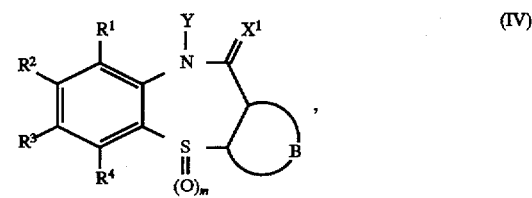

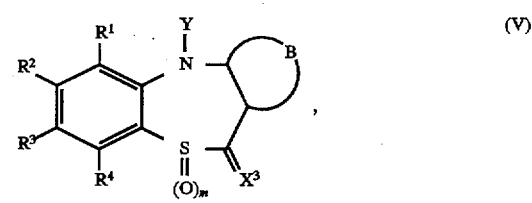

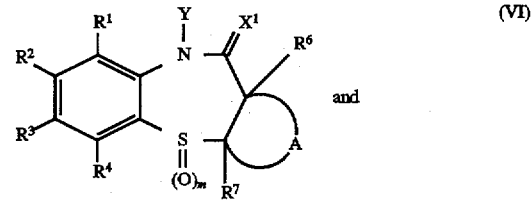

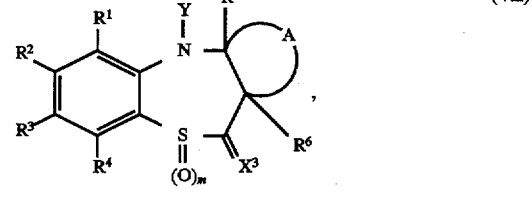

where $R^1$, $R^2$, $R^3$, $R^4$ are identical or different and represent hydrogen, hydroxy, amino, cyano, halogen, nitro, nitroso, sulphonyl, sulphoxyl, tosyl, mercapto, carboxyl, carboxamido, carbalkoxy, dithiocarboxyl, thiocarboxamido, dithiocarbalkoxy, optionally substituted alkyl, aryl, heteroaryl, alkoxy, aryloxy, heteroaryloxy, acyloxy, alkylthio, arylthio, heteroarylthio, acylthio, acyl, thioacyl or acylamino or among one another form one or more saturated or unsaturated, optionally substituted isocyclic or heterocyclic carbon rings having up to 8 carbon atoms, Y is hydrogen, optionally substituted alkyl, aryl, heteroaryl, acyl, thioacyl, acyloxy, arylamino or acylamino, $X^1$, $X^2$ or $X^3$ is one of the following groups:

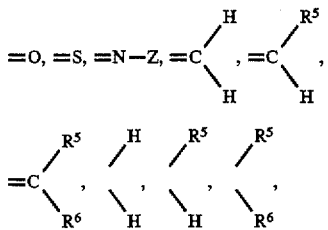

$R^5$, $R^6$ and $R^7$ are identical or different and are as defined for $R^1$ to $R^4$, except that among one another they are not able to form a cyclic ring, Z is as defined for Y with the exception that Z cannot be H, A indicates the fusion of an optionally substituted saturated isocyclic or heterocyclic ring having up to 8 carbon atoms, B indicates the fusion of an optionally substituted unsaturated isocyclic or heterocyclic ring having up to 8 carbon atoms and m is 0 or 1, cyclic benzo-condensed imines of the formula

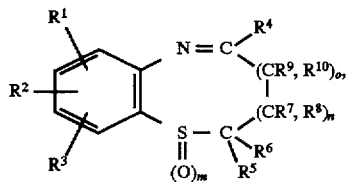

(VIII)

where $R^1$ and $R^2$ are, independently of one another, hydrogen, hydroxy, amino, cyano, halogen, nitro, carboxyl, halogenocarbonyl, carboxamido, alkoxycarbonyl, alkyl, aryl, alkoxy, aryloxy, acyloxy, alkylthio, arylthio, acylthio, acyl, thioacyl or acylamino, $R^3$ represents hydrogen or chlorine and can furthermore, together with one of the radicals $R^1$ or $R^2$ in the case of adjacent substitution and together with the substituted carbon atoms, form a fused saturated, unsaturated or aromatic, isocyclic or heterocyclic 5–8-membered ring, $R^4$ is hydrogen, alkyl, aryl, halogen, alkylthio, arylthio, alkoxy, aryloxy, amino, hydrazino, alkylhydrazino or phenylhydrazino, m, n and o can assume, independently of one another, the value 0 or 1, $R^6$, $R^8$ and $R^9$ are, independently of one another, hydrogen, alkyl, alkoxy, phenyl, acyloxy, cyano, halogen, carboxyl, alkoxycarbonyl, phenoxy or acyl and $R^6$, $R^8$ and $R^{10}$ are, independently of one another, hydrogen, alkyl or halogen, where $R^5$ and $R^7$ or $R^7$ and $R^9$ together with the substituted carbon atoms can represent a saturated, unsaturated or aromatic isocyclic or heterocyclic 5–8-membered ring and where furthermore $R^6$ and $R^8$ or $R^8$ and $R^{10}$ can together form a double bond and where furthermore $R^5$ and $R^6$ can together represent doubly bonded oxygen, sulphur or $R^{11}$-substituted nitrogen, where $R^{11}$ is alkyl, aryl, acyl, alkylamino or arylamino, benzo[f]-1,4-thiazepines of the formula

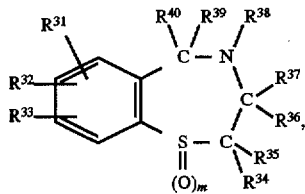

(IX)

where $R^{31}$ and $R^{32}$ are, independently of one another, hydrogen, hydroxy, amino, cyano, halogen, nitro, $C_1$-$C_8$-alkyl, unsubstituted phenyl or phenyl substituted by $R^{31}$ and $R^{32}$ (with the exception of resubstitution by $R^{31}$- and $R^{32}$-substituted phenyl), $C_1$-$C_8$-alkoxy, phenoxy, $C_1$-$C_8$-acyloxy, $C_1$-$C_8$-acyl or $C_1$-$C_8$-alkoxycarbonyl, $R^{33}$ represents hydrogen or chlorine and can furthermore, together with one of the radicals $R^{31}$ or $R^{32}$ and together with the substituted carbon atoms, form a fused saturated, unsaturated or aromatic isocyclic or heterocyclic 5–8-membered ring, $R^{34}$, $R^{36}$ and $R^{40}$ are, independently of one another, hydrogen, $C_1$-$C_8$-alkyl, unsubstituted phenyl or phenyl substituted by $R^{31}$ and $R^{32}$ (with the exception of resubstitution by $R^{31}$- and $R^{32}$-substituted phenyl), $C_1$-$C_8$-acyl, $C_1$-$C_8$-alkoxycarbonyl, cyano, halogen, carboxyl, $C_1$-$C_8$-alkoxy, $C_1$-$C_8$-alkylthio, phenylthio, benzylthio, phenoxy or $C_1$-$C_8$-acyloxy, $R^{35}$, $R^{37}$ and $R^{39}$ are, independently of one another, hydrogen, $C_1$-$C_8$-alkyl, halogen, $C_1$-$C_8$-alkoxy or $C_1$-$C_8$-alkylthio, $R^{38}$ is hydrogen, $C_1$-$C_8$-alkyl, unsubstituted phenyl or phenyl substituted by $R^{31}$ and $R^{32}$ (with the exception of resubstitution by $R^{31}$- and $R^{32}$-substituted phenyl), $C_1$-$C_8$-acyl, $C_1$-$C_8$-thioacyl, halogenocarbonyl or $C_1$-$C_8$-alkoxycarbonyl and p represents the number 0 or 1, where furthermore the substituent pairs $R^{34}$ and $R^{35}$, $R^{36}$ and $R^{37}$ and also $R^{39}$ and $R^{40}$ can be, independently of one another, doubly bonded oxygen, sulphur or $R^{38}$-substituted nitrogen and where furthermore the substituent pairs $R^{35}$ and $R^{36}$ and also $R^{38}$ and $R^{39}$ can, independently of one another, form a double bond and where furthermore the substituent pairs $R^{34}$ and $R^{37}$ and also $R^{38}$ and $R^{39}$ can, independently of one another, form 3- to 5-membered alkylene, in which 1 or 2 carbon atoms can be replaced by oxygen, sulphur or $R^{38}$-substituted nitrogen, and where furthermore $R^{40}$ can also be hydrazino, $C_1$-$C_8$-alkylhydrazino or phenyl-hydrazino, cyclic amidines oxy-substituted on the exocylic nitrogen atom of the formula

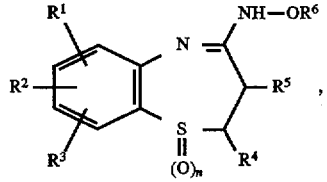

(X)

where $R^1$ and $R^2$ are, independently of one another, hydrogen, cyano, halogen, carboxyl, alkoxycarbonyl, alkyl, aryl, alkoxy, aryloxy or acyl, $R^3$ represents hydrogen, alkyl or chlorine and furthermore can, together with one of the radicals $R^1$ or $R^2$ in the case of adjacent substitution and together with the substituted carbon atoms, form a fused saturated, unsaturated or aromatic, isocyclic or heterocyclic 5–8-membered ring, R⁴ and R⁵ are, independently of one another, hydrogen, alkyl, aryl, halogen, alkoxy, aryloxy, acyl or acyloxy or together with the substituted carbon atoms can form a saturated or unsaturated, isocyclic or heterocyclic 5–8-membered ring, R⁶ is hydrogen, alkyl, aryl or silyl substituted by alkyl or aryl and n can assume the value 0 or 1, 1,6-benzo-thioazocines of the formula

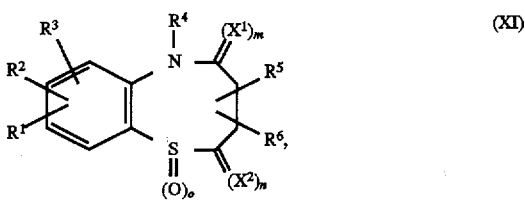

(XI)

where

R¹ and R² are, independently of one another, hydrogen, hydroxyl, amino, cyano, halogen, nitro, alkylsulphonyl, phenylsulphonyl, alkylsulphoxyl, phenylsulphoxyl, tosyl, mercapto, carboxyl, halogenocarbonyl, carboxamido, alkoxycarbonyl, thiocarboxamido, alkyl, aryl, heteroaryl, alkoxy, aryloxy, heteroaryloxy, acyloxy, alkylthio, arylthio, heteroarylthio, acylthio, acyl, thioacyl or acylamino, R³ represents hydrogen or chlorine and can furthermore, together with one of the radicals R¹ or R² and together with the substituted carbon atoms, form a fused saturated, unsaturated or aromatic, isocyclic or heterocyclic 5–8-membered ring, R⁴ is hydrogen, alkyl, aryl, heteroaryl, acyl, thioacyl, halogenocarbonyl or alkoxycarbonyl, X¹ and X² represent, independently of one another, doubly bonded oxygen, sulphur or R⁷-substituted nitrogen, where R⁷ is as defined for R⁴ with the exception of hydrogen, m, n and o can, independently of one another, assume the value 0 or 1 and R⁵ and R⁶ can, independently of one another, be positioned on one or on two of the carbon atoms located between the sulphur atom and the nitrogen atom in the 8-membered ring, if these carbon atoms are not occupied by X¹ or X², and are as defined as for R¹ and R², where in the case of adjacent substitution a saturated, unsaturated or aromatic isocyclic or heterocyclic 5–8-membered ring can also be formed together with the substituted carbon atoms and where furthermore the definition of the doubly bonded oxygen or sulphur can be assumed and N-substituted phenothiazine derivatives of the formula

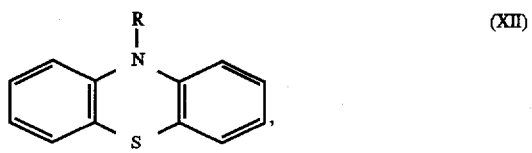

(XII)

where

R is an aryl radical or

—C—R¹,
|
R² where

R¹ is =O, =S,

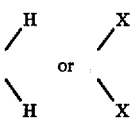

and

X is Br or Cl and

R² is an aryl radical, Br, Cl or the radical —CH$_x$X$_y$, where

X is Br or Cl, x is a value from 0 to 2, y is a value from 1 to 3 and x+y=3 or where R is a CF$_3$—(CF$_2$)$_n$—CO radical, where n represents zero, 1 or 2.

Preference is given to using 1,4-thiazepine derivatives and dibenzo-1,4-thiazine derivatives, particularly preferably benzo[b]-1,4-thiazepine derivatives and N-perfluoroacyl-substituted phenothiazines. In both stages of the process, it is possible to use the same cocatalyst, but also different cocatalysts. Moreover, it is also possible to use mixtures of the specified cocatalysts in both stages.

In the first reaction stage, for example, from 0.005 to 0.75% by weight of cocatalyst (based on 3-fluorotoluene) can be used. This amount is preferably from 0.05 to 0.5% by weight. In the second reaction stage, for example, a further 0.1 to 5% by weight of cocatalyst (based on 3-fluorotoluene) can be added. This additional amount is preferably from 0.3 to 2% by weight.

Both reaction stages of the process of the invention can be carried out in the presence or absence of solvents. Suitable solvents are, for example, halogenated C$_1$-C$_4$-hydrocarbons such as carbon tetrachloride or dichloromethane and, particularly for the second reaction stage, also longer-chain halogenated aliphatic hydrocarbons having correspondingly higher boiling points. Both reaction stages are preferably carried out without addition of solvent.

The first reaction stage can be carried out, for example, at from 0° to 50° C. and, for example, from 0.8 to 1.1 mol of chlorine can be passed in per mole of 3-fluorotoluene. Preferably, the first reaction stage is carried out at from 10° to 30° C. and from 0.95 to 1.01 mole of chlorine are passed in per mole of 3-fluorotoluene. Particularly preferably, the reaction is carried out at room temperature and 1 mol of chlorine is passed in per mole of 3-fluorotoluene.

The second reaction stage can be carried out, for example, at from 60° to 120° C. and, for example, from 0.8 to 1.0 mol of chlorine can be passed in per mole of 3-fluorotoluene. Preferably, this reaction stage is carded out at from 70° to 100° C. and from 0.95 to 0.98 mol of chlorine is passed in per mole of 3-fluorotoluene.

In carrying out the first and second reaction stages of the process of the invention, the pressure can in each case be, for example, in the range from 1 to 10 bar. Preference is given to atmospheric pressure.

In both reaction stages, the elemental chlorine can be passed in in gaseous or liquid form.

The reaction mixture present after completion of the second reaction stage can be worked up, for example, by separating off the catalysts, for example by filtration, and blowing out any hydrogen chloride present. The generally less valuable Friedel-Crafts catalyst can also be removed by washing with water once or a plurality of times and then working up the remaining reaction mixture by distillation. The more valuable cocatalysts here remain in the distillation residue and can be reused in the form of this residue or after work-up.

The separation of the two isomers present in the reaction mixture (3-fluoro-4,6-dichlorotoluene and 3-fluoro-2,6-dichlorotoluene) is possible by methods known per se, for example by distillation. If the 3-fluoro-4,6-dichlorotoluene is to be used for preparing 3-fluoro-4,6-dichlorobenzoyl chloride therefrom, the isomer separation can also be carried out only after the side-chain chlorination from the benzal chloride/beazotrichloride mixture then present.

It is extremely surprising that the two-stage process of the invention gives reaction mixtures having a significantly increased content of 3-fluoro-4,6-dichlorotoluene than a corresponding single-stage process in which the entire chlorination is carried out under the same reaction conditions and without further addition of catalysts.

The process of the invention for preparing 3-fluoro-4,6-dichlorotoluene has a series of advantages. Thus, in conventional industrial plants and using customary chemicals, it can give 3-fluoro-4,6-dichlorotoluene in amounts which are as large as desired. Moreover, it is substantially simpler technically than known processes and does not require use of materials which are difficult to handle. Finally, it is also an advantage that the valuable cocatalysts can be reused. Overall, the process of the invention provides a very favourable route for preparing an important intermediate for active compounds from the group of quinolonecarboxylic acids.

The following examples illustrate the invention.

EXAMPLES

All percentages are by weight.

Example 1

A chlorination vessel was charged with 275 g of 3-fluorotoluene, 0.55 g of iron(III) chloride and 0.90 g of N-trifluoroacetylphenothiazine and, at 20° C. while stirring, 178 g of chlorine were passed in uniformly over the course of 6 hours. After 15 minutes of further stirring, 1.53 g of iron(III) chloride and 2.18 g of N-trifluoroacetylphenothiazine were added, the mixture was heated to 80° C. and, at this temperature while stirring, a further 179 g of chlorine were passed in uniformly over the course of 6 hours. The product mixture obtained was analysed by means of GC. It contained 1.3% of 3-fluoro-6-chlorotoluene, 75.0% of 3-fluoro-4,6-dichlorotoluene and 20.3% of 3-fluoro-2,6-dichlorotoluene. This gives a formation selectivity for 3-fluoro-4,6-dichlorotoluene of 76%.

Example 2

Example 1 was repeated, but 0.30 g of 2,3-dihydroxybenzo-[b]-1,4-thiazepin-5-one was used in the 2nd stage in place of 2.18 g of N-trifluoroacetylplxenothiazine. The product mixture obtained contained, according to GC analysis, 2.0% of 3-fluoro-6-chlorotoluene, 72.0% of 3-fluoro-4,6-dichlorotoluene and 22.1% of 3-fluoro-2,6-dichlorotoluene, corresponding to a formation selectivity for 3-fluoro-4,6-dichlorotoluene of 73.5%.

Example 3 (for comparison)

A chlorination vessel was charged with 275 g of 3-fluorotoluene, 2.55 g of iron(III) chloride and 2.90 g of N-trifluoroacetylphenothiazine and, at 80° C., 256 g of chlorine were passed in uniformly over the course of 15 hours. The product mixture obtained contained, according to GC analysis, 2.5% of 3-fluoro-6-chlorotoluene. The formation selectivity for 3-fluoro-4,6-dichlorotoluene was only 65.3%.

Example 4 (for comparison)

Example 3 was repeated, but using 0.60 g of 2,3-dihydrobenzo-[b]-1,4-thiazepin-5-one in place of 2.90 g of N-trifluoroacetylphenothiazine. The product mixture obtained contained, according to GC analysis, 10.3% of 3-fluoro-6-chlorotoluene: The formation selectivity for 3-fluoro-4,6-dichlorotoluene was only 59.8%.

What is claimed is:

1. In the preparation of 3-fluoro-4,6-dichlorotoluene by chlorinating 3-fluorotoluene with chlorine in the presence of a catalyst, the improvement which comprises effecting the chlorination in two stages, the temperature in the first stage ranging from 0° to 50° C. and in the second stage ranging from 60° to 120° C., in the first reaction stage there being added 0.05 to 1% by weight of a Friedel-Crafts-catalyst and 0.005 to 0.75% by weight of a heterocyclic co-catalyst, and additionally to the second stage 0.1 to 5% by weight of a Friedel-Crafts-catalyst and 0.1 to 5% by weight of a heterocyclic co-catalyst (all amounts of catalysts being based on 3-fluoro-toluene) wherein the co-catalyst used is selected from the group consisting of thiazepines of the formula

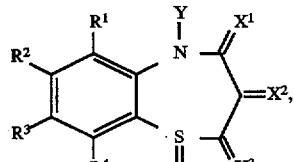

(I)

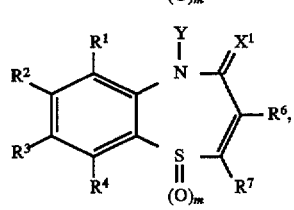

(II)

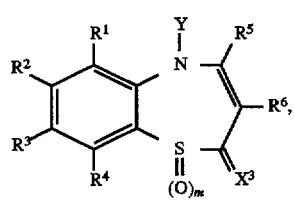

(III)

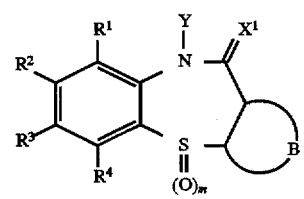

(IV)

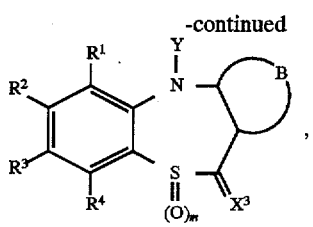

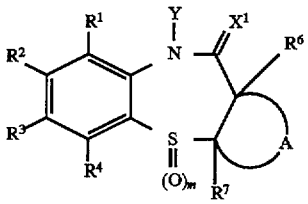

and

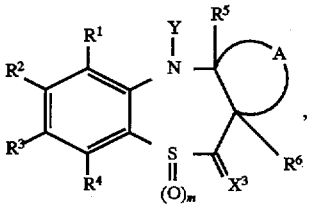

where

R¹, R², R³, R⁴ are identical or different and represent hydrogen, hydroxy, amino, cyano, halogen, nitro, nitroso, sulphonyl, sulphoxyl, tosyl, mercapto, carboxyl, carboxamido, carbalkoxy, dithiocarboxyl, thiocarboxamido, dithiocarbalkoxy, optionally substituted alkyl, aryl, heteroaryl, alkoxy, aryloxy, heteroaryloxy, acyloxy, alkylthio, arylthio, heteroarylthio, acylthio, acyl, thioacyl or acylamino or among one another form one or more saturated or unsaturated, optionally substituted isocyclic or heterocyclic carbon rings having up to 8 carbon atoms, Y is hydrogen, optionally substituted alkyl, aryl, heteroaryl, acyl, thioacyl, acyloxy, arylamino or acylamino, X¹, X² or X³ is one of the following groups:

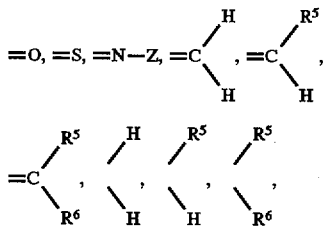

R⁵, R⁶ and R⁷ are identical or different and are as defined for R¹ to R⁴, except that among one another they are not able to form a cyclic ring, Z is as defined for Y with the exception that Z cannot be H, A indicates the fusion of an optionally substituted saturated isocyclic or heterocyclic ring having up to 8 carbon atoms, B indicates the fusion of an optionally substituted unsaturated isocyclic or heterocyclic ring having up to 8 carbon atoms and m is 0 or 1, cyclic benzo-condensed imines of the formula

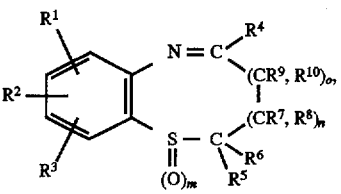

where

R¹ and R² are, independently of one another, hydrogen, hydroxy, amino, cyano, halogen, nitro, carboxyl, halogenocarbonyl, carboxamido, alkoxycarbonyl, alkyl, aryl, alkoxy, aryloxy, acyloxy, alkylthio, arylthio, acylthio, acyl, thioacyl or acylamino, R³ represents hydrogen or chlorine and can furthermore, together with one of the radicals R¹ or R² in the case of adjacent substitution-and together with the substituted carbon atoms, form a fused saturated, unsaturated or aromatic, isocyclic or heterocyclic 5–8-membered ring, R⁴ is hydrogen, alkyl, aryl, halogen, alkylthio, arylthio, alkoxy, aryloxy, amino, hydrazino, alkylhydrazino or phenylhydrazino, m, n and o can assume, independently of one another, the value 0 or 1, R⁵, R⁷ and R⁹ are, independently of one another, hydrogen, alkyl, alkoxy, phenyl, acyloxy, cyano, halogen, carboxyl, alkoxycarbonyl, phenoxy or acyl and R⁶, R⁸ and R¹⁰ are, independently of one mother, hydrogen, alkyl or halogen, where R⁵ and R⁷ or R⁷ and, R⁹ together with the substituted carbon atoms can represent a saturated, unsaturated or aromatic isocyclic or heterocyclic 5–8-membered ting and where furthermore R⁶ and R⁸ or R⁸ and R¹⁰ can together form a double bond and where furthermore R⁵ and R⁶ can together represent doubly bonded oxygen, sulphur or R¹¹-substituted nitrogen, where R¹¹ is alkyl, aryl, acyl, alkylamino or arylamino, benzo[f]-1,4-thiazepines of the formula

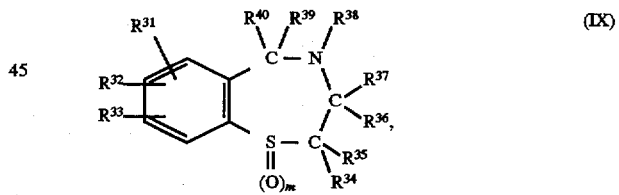

where

R³¹ and R³² are, independently of one another, hydrogen, hydroxy, amino, cyano, halogen, nitro, C₁–C₈-alkyl, unsubstituted phenyl or phenyl substituted by R³¹ and R³² (with the exception of resubstitution by R³¹- and R³²-substituted phenyl), C₁–C₈-alkoxy, phenoxy; C₁–C₈-acyloxy, C₁–C₈-acyl or C₁–C₈-alkoxycarbonyl, R³³ represents hydrogen or chlorine and can furthermore, together with one of the radicals R³¹ or R³² and together with the substituted carbon atoms, form a fused saturated, unsaturated or aromatic isocyclic or heterocyclic 5–8-membered ring, R³⁴, R³⁶ and R⁴⁰ are, independently of one another, hydrogen, C₁–C₈-alkyl, unsubstituted phenyl or phenyl substituted by R³¹ and R³² (with the exception of resubstitution by R³¹- and R³²-substituted phenyl), C₁–C₈-acyl, C₁–C₈-alkoxycarbonyl, cyano, halogen, carboxyl, $C_1$–$C_8$-alkoxy, $C_1$–$C_8$-alkylthio, phenylthio, benzylthio, phenoxy or $C_1$–$C_8$-acyloxy, $R^{35}$, $R^{37}$ and $R^{39}$ are, independently of one another, hydrogen, $C_1$–$C_8$-alkyl, halogen, $C_1$–$C_8$-alkoxy or $C_1$–$C_8$-alkylthio, $R^{38}$ is hydrogen, $C_1$–$C_8$-alkyl, unsubstituted phenyl or phenyl substituted by $R^{31}$ and $R^{32}$ (with the exception of resubstitution by $R^{31}$- and $R^{32}$-substituted phenyl), $C_1$–$C_8$-acyl, $C_1$–$C_8$-thioacyl, halogenocarbonyl or $C_1$–$C_8$-alkoxycarbonyl and p represents the number 0 or 1, where furthermore the substituent pairs $R^{34}$ and $R^{35}$, $R^{36}$ and $R^{37}$ and also $R^{39}$ and $R^{40}$ can be, independently of one another, doubly bonded oxygen, sulphur or $R^{38}$-substituted nitrogen and where furthermore the substituent pairs $R^{35}$ and $R^{36}$ and also $R^{38}$ and $R^{39}$ can, independently of one another, form a double bond and where furthermore the substituent pairs $R^{34}$ and $R^{37}$ and also $R^{38}$ and $R^{39}$ can, independently of one another, form 3- to 5-membered alkylene, in which 1 or 2 carbon atoms can be replaced by oxygen, sulphur or $R^{38}$-substituted nitrogen, and where furthermore $R^{40}$ can also be hydrazino, $C_1$–$C_8$-alkylhydrazino or phenyl-hydrazino, cyclic amidines oxy-substituted on the exocylic nitrogen atom of the formula

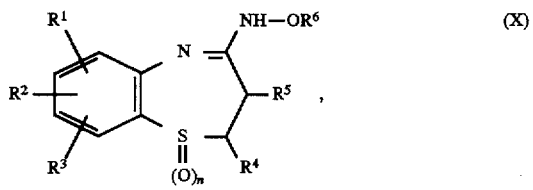

where $R^1$ and $R^2$ are, independently of one another, hydrogen, cyano, halogen, carboxyl, alkoxycarbonyl, alkyl, aryl, alkoxy, aryloxy or acyl, $R^3$ represents hydrogen, alkyl or chlorine and furthermore can, together with one of the radicals $R^1$ or $R^2$ in the case of adjacent substitution and together with the substituted carbon atoms, form a fused saturated, unsaturated or aromatic, isocyclic or heterocyclic 5–8-membered ring, $R^4$ and $R^5$ are, independently of one another, hydrogen, alkyl, aryl, halogen, alkoxy, aryloxy, acyl or acyloxy or together with the substituted carbon atoms can form a saturated or unsaturated, isocyclic or heterocyclic 5–8-membered ring, $R^6$ is hydrogen, alkyl, aryl or silyl substituted by alkyl or aryl and n can assume the value 0 or 1, 1,6-benzo-thioazocines of the formula

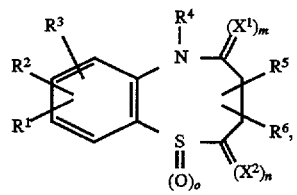

where $R^1$ and $R^2$ are, independently of one another, hydrogen, hydroxyl, amino, cyano, halogen, nitro, alkylsulphonyl, phenylsulphonyl, alkylsulphoxyl, phenylsulphoxyl, tosyl, mercapto, carboxyl, halogenocarbonyl, carboxamido, alkoxycarbonyl, thiocarboxamido, alkyl, aryl, heteroaryl, alkoxy, aryloxy, heteroaryloxy, acyloxy, alkylthio, arylthio, heteroarylthio, acylthio, acyl, thioacyl or acylamino, $R^3$ represents hydrogen or chlorine and can furthermore, together with one of the radicals $R^1$ or $R^2$ and together with the substituted carbon atoms, form a fused saturated, unsaturated or aromatic, isocyclic or heterocyclic 5–8-membered ring, $R^4$ is hydrogen, alkyl, aryl, heteroaryl, acyl, thioacyl, halogenocarbonyl or alkoxycarbonyl, $X^1$ and $X^2$ represent, independently of one another, doubly bonded oxygen, sulphur or $R^7$-substituted nitrogen, where $R^7$ is as defined for $R^4$ with the exception of hydrogen, m, n and o can, independently of one another, assume the value 0 or 1 and $R^5$ and $R^6$ can, independently of one another, be positioned on one or on two of the carbon atoms located between the sulphur atom and the nitrogen atom in the 8-membered flag, if these carbon atoms are not occupied by $X^1$ or $X^2$, and are as defined as for $R^1$ and $R^2$, where in the case of adjacent substitution a saturated, unsaturated or aromatic isocyclic or heterocyclic 5–8-membered ring can also be formed together with the substituted carbon atoms and where furthermore the definition of the doubly bonded oxygen or sulphur can be assumed and N-substituted phenothiazine derivatives of the formula

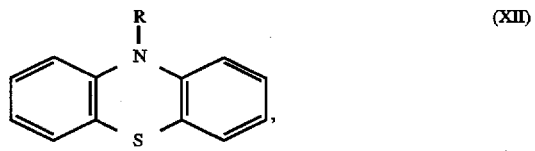

where

R is an aryl radical or

where $R^1$ is =O, =S,

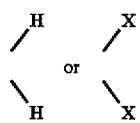

and
X is Br or Cl and
$R^2$ is an aryl radical, Br, Cl or the radical —$CH_xX_y$,
where
X is Br or Cl,
x is a value from 0 to 2,
y is a value from 1 to 3 and
x+y=3 or
where
R is a $CF_3$—$(CF_2)_n$—CO radical; Where
n represents zero, 1 or 2.

2. The process of claim 1, in which the Friedel-Crafts catalysts used are selected from the group consisting of iron(III) chloride, antimony(III) chloride, antimony(V) chloride and aluminium chloride.

3. The process of claim 1, in which the cocatalysts used are heterocycles which contain both nitrogen and sulphur atoms and belong to the classes of the thiazines, thiazepines or thiazocines.

4. The process of claim 1, in which the cocatalysts used are selected from the group consisting of benzo[b]-1,4-thiazepine derivatives and N-perfluoroacyl-substituted phenothiazines.

5. The process of claim 1, in which the cocatalysts used are selected from the group consisting of N-trifluoroacetylphenothiazine and 2,3-dihydrobenzo[b]-1,4-thiazepin-5-one.

6. The process of claim 1, in which in the first reaction stage from 0.8 to 1.1 mol of chlorine is passed in per mole of 3-fluorotoluene and in the second reaction stage from 0.8 to 1.0 mol of chlorine is passed in per mole of 3-fluorotoluene.

7. The process of claim 1, in which the reaction mixture present after completion of the second reaction stage is worked up by distillation and the cocatalysts obtained in the distillation residue are reused.

* * * * *

UNITED STATES PATENT AND TRADEMARK OFFICE
CERTIFICATE OF CORRECTION

PATENT NO. : 5,684,217
DATED : November 4, 1997
INVENTOR(S) : Mais, et al.

It is certified that error appears in the above-indentified patent and that said Letters Patent is hereby corrected as shown below:

Col. 9, line 55     After " $R^6$ " delete " and R7 " and substitute -- and $R^7$ --

Col. 10, line 31     Delete " mother " and substitute -- another --

Col. 12, line 40     Delete " flag " and substitute -- ring --

Signed and Sealed this

Eighteenth Day of August, 1998

Attest:

BRUCE LEHMAN

*Attesting Officer*     *Commissioner of Patents and Trademarks*